United States Patent [19]

Fischer

[11] Patent Number: 5,876,932

[45] Date of Patent: Mar. 2, 1999

[54] METHOD FOR GENE EXPRESSION ANALYSIS

[75] Inventor: Achim Fischer, Freiburg, Germany

[73] Assignee: Max-Planc-Gesellschaft zur Forderung der Wissenschaften e V. Berlin, Munich, Germany

[21] Appl. No.: 649,511

[22] Filed: May 17, 1996

[30] Foreign Application Priority Data

May 19, 1995 [DE] Germany ........................ 195 18 505.6

[51] Int. Cl.[6] .............................. C12Q 1/68; C12P 19/34
[52] U.S. Cl. ............................... 435/6; 435/91.2
[58] Field of Search ......................... 536/23.1; 435/91.1, 435/91.2, 91.3, 6

[56] References Cited

U.S. PATENT DOCUMENTS 4,683,195  7/1987  Mullis et al. ............................... 435/6

OTHER PUBLICATIONS

Zakut et al., "Differential Expression of MAGE–1, –2, and –3 Messenger RNA in Transformed and Normal Human Cell Lines," *Cancer Research*, 53:5–8 (1993).

Mohaupt et al., "Differential Expression and Induction of mRNAs Encoding Two Inducible Nitric Oxide Synthases in Rat Kidney," *Kidney International*, 46:653–665 (1994).

Promega Protocols and Applications Guide, Promega Corp. 1991, 2nd Edition.

Song, K, et al. 1994, Plant Molecular Biology, vol 26, pp. 1065–1071.

Baier, G, et al. 1993. Nucleic Acids Research, vol 21, No 5 pp. 1329–1330.

Frohman, M. et al. 1988, PNAS vol 85, pp. 8998–9002.

Bhat, et al 1991, Nucleic Acids Research, vol 19. No 2 p. 398.

Sommer, S. et al., in PCR Protocols: A guide to Methods and Applications, Michael Innis, editor, Academic Press, Chapter 25.

Feng et al. FEBS vol. 282 (1) pp. 98–102, 1991.

Abe et al. FEBS vol. 316 (3) pp. 253–256, 1993.

*Primary Examiner*—James Ketter
*Assistant Examiner*—Irem Yucel
*Attorney, Agent, or Firm*—Fulbright & Jaworski, LLP

[57] ABSTRACT

The present invention concerns a method for the general analysis of gene expression as well as a method for the differential analysis of the expression of members of a gene family.

67 Claims, 6 Drawing Sheets

FIG. 6

```
                    1                                                       60
MADS-CONSENSUS: MGRGKIEIKB IENKTNRQVT FSKRRNGLLK KAYELSVLCD AEVALIIFSS RGKLYEYASN

AGAMOUS (At):   S--------- ---T------ ---------- -C-------- ------V--- -R------SN-
FBP6    (Ph):   S--------- ---T------ ---------- -C-------- ------V--- -R-------N-
TAG1    (Le):   L--------- ---T------ ---------- -C-------- -----VV--N -R-------N-
ZAG1    (Zm):   R-K--T---- ---T------ ---------- -C-------- ------V--- -R-------N-    AG
ZMM2    (Zm):   ---------- T-S------- ---------- -C-------- -----VV--- -R-------N-
ZAG2    (Zm):   ----R----- ---N-S---- ---------- -C-------- ------V--- -R-------N-
ZMM1    (Zm):   ----R----- ---N-S---- ---------- -C-------- -----VV--- -R-------N-

AGL2    (At):   ----RV-L-- ----I----- ---------- -A-------- ---------N ------FC-S
FBP2    (Ph):   ----RV-L-- ----I----- ---------- -A-------- ---------N ------FC-S
TMS     (Le):   ----RV-L-- ---G-I---- ---------- -A-------- ---------N ------FC-S    AGL2
ZMM7    (Zm):   ---------- ----I----- ---------- -A-------- ---------N ------FC-G
ZMM3    (Zm):   ---------- ---IS----- ---------- -A-------- ---------- ----R-F-FSTS
```

METHOD FOR GENE EXPRESSION ANALYSIS

DESCRIPTION

The present invention concerns a method for the general gene expression analysis as well as a method for the differential analysis of the expression of members of a gene family.

The molecular basis for numerous biological processes is the coordinated activation or inactivation of particular genes or groups of genes in a cell, an organ or an organism. In this process the cell, the organ or the organism is in a particular physiological state, a degree of differentiation and in the case of certain external influences characterized by a specific expression status. Knowledge of this expression status i.e. the degree of activation of all genes or particular groups of genes is of key importance for answering many biological questions. Thus the aim of a method by which it is intended to obtain information about the expression status, is therefore on the one hand to determine the activity of all genes as well as the activity of a particular subset of genes. Gene families come in particular into consideration as subsets. Gene families are groups of genes which are often functionally characterized by a particular type of function which the gene products in a cell undertake and which structurally have one or several conserved regions (domains) in common. Examples of gene families are the MADS-box and the homoebox gene family as well as further transcription factor families. The cyclin, cytokine and globin gene families are for example of medical interest.

The analysis of the expression status of genes is known from the state of the art. Differential display RT-PCR (DDRT) is for example a method for analysing differential gene expression in which mRNA from a tissue is transcribed by using a cDNA primer with a 3' extension (preferably two bases) by reverse transcription (RT) into (preferably 12) subpopulations of cDNA. PCR products with transcript-specific lengths which can be separated on sequencing gels are produced from this cDNA by using short primers, preferably of 10 nucleotides in length, with a random sequence. If the number of primer combinations used is large enough it is possible statistically to detect almost all transcripts present in the tissue. If the PCR products obtained from two or more tissues are applied next to one another on a gel, it is possible to directly display expression differences in this manner. Bands which appear differentially can be cut out of the gel, reamplified and cloned for further analysis.

In addition in order to enrich the amplification products for a particular subgroup of all mRNA molecules, e.g. members of a particular gene family, it is possible to combine a primer which has a sequence specific for a gene family with a random primer. This technique of DDRT is described for example by Liang and Pardee (1992) Science 257, 967–971; Liang et al (1993), Nucleic Acids Res. 21, 3269–3275; Bauer et al (1993) Nucleic Acids Res. 21, 4272–4280; Stone and Wharton (1994), Nucleic acid Res. 22, 2612–2618 and Wang and Feuerstein (1995) Biotechniques 18, 448–452 and WO 93/18176 and DE 43 17 414.

However, the experimental design of DDRT leads to a series of disadvantages. Thus the band pattern is often only poorly reproducible. Even the use of longer random primers of e.g. 20 bases in length was not able to satisfactorily solve the problem of reproducibility (Ito et al., (1994), FEBS Lett. 351, 231–236). In addition an extremely large amount of work is necessary due to the high number of necessary primer combinations and to the necessity of having to increase the reproducibility by replicates. In addition one often obtains a high proportion of false positive results. Moreover it has also been shown that rare transcripts cannot be detected in many DDRT experiments (Bertioli et al. (1995), Nucleic Acids Res. 23, 4520–4523).

The sequencing of selected bands described in the state of the art is also problematic since DDRT products are often flanked by the same primer at both ends so that direct sequencing is not possible and an additional cloning step is necessary. Due to the use of short primers, a further reamplification step with primer molecules extended on the 5' side compared to the DDRT primers is necessary even if the product is flanked by two different primers. Finally due to the use of random primers it is never quite possible to be sure that all transcripts of a cell are recognized by the primer combinations used. This applies—even when using a high number of primers—to an experiment which is intended to detect the entirety of all transcripts as well as to an experiment which is directed towards the analysis of a subpopulation of transcripts such as a gene family.

Song and Osborn describe a method in Plant Molecular Biology 26 (1994), 1065–1071, for examining the expression of homologous genes in plant polyploids in which the techniques of RT-PCR and RFLP (restriction fragment length polymorphism) analysis are combined with one another. In this method a cDNA is produced from RNA by reverse transcription which is amplified by using two gene-specific primers. The amplification products are transcript-specifically shortened by endonuclease cleavage, they are separated according to their length and analysed by subsequent cloning and sequencing. This method also has the disadvantage of low sensitivity since an additional cloning step is necessary to identify the expression products. A further disadvantage of this method is that gene specific sequence information must be available on at least two regions within the analysed genes in order to design suitable primers.

The object of the present invention was therefore to provide a method for gene expression analysis in which the disadvantages of the state of the art can be at least partially avoided and in particular a method in which reproducible results are obtained, which has an adequate sensitivity in order to also detect rare transcripts and which enables an identification of amplification products without an additional cloning step.

This object is achieved in a first embodiment of the present invention by providing a method for the differential analysis of gene expression of members of a gene family characterized by the steps:

(a) isolation of mRNA molecules from one or several tissue samples to be analysed, (b) synthesising cDNA first strand molecules from the mRNA molecules, (c) selective amplification of the cDNA first strand molecules of members of a gene family of interest in which at least one primer specific for the gene family is used which is an oligonucleotide or a mixture of oligonucleotides with a sequence which can hybridize with a conserved domain within the gene family of interest and labelling of the amplification products, (d) transcript-specific shortening of the amplification products by cleavage with one or several restriction endonucleases, (g) separation of the amplification products according to their length and (h) analysis of the separated amplification products.

In a second embodiment of the present invention a further method for analysing the expression of members of a gene family is provided characterized by the steps:

(a) isolation of mRNA molecules from one or several tissue samples to be analysed (b) synthesising cDNA first strand molecules from the mRNA molecules (c) selective amplification of the cDNA first strand molecules of members of a gene family of interest in which at least one primer specific for the gene family is used which is an oligonucleotide or a mixture of oligonucleotides with a sequence which can hybridize with a conserved domain within the gene family of interest, (d) transcript-specific shortening of the amplification products by cleavage with one or several restriction endonucleases, (e) attachment of linker molecules to the ends of the restriction fragments, (f) reamplification and labelling of the restriction fragments in which a primer directed against the linker molecule and a gene family-specific primer are used, (g) separation of the reamplification products according to their length and (h) analysis of the separated reamplification products.

A modification of the first and second embodiment of the method according to the invention is to replace the primer specific for a gene family by a set of random primers—corresponding to the DD method—in order to enable not only a test for members of a gene family but a test for any arbitrary transcripts. In this modification degenerate random primers which for example have a length of ca. 15 to 25 nucleotides are preferably used. These degenerate random primers particularly preferably have an adequately high degree of degeneracy in order to statistically bind to a DNA template as frequently as an 8 to 12 nucleotide longer non-degenerate primer. The degree of degeneracy of the random primer can be achieved by using oligonucleotide mixtures or/and by incorporating degenerate hybridizing nucleotides such as inosine.

A further modification of the first and second embodiment of the method according to the invention is to replace during the first round of amplification the primer specific for a gene family by a primer directed against a specific sequence attached to the 5' end of the mRNA or the 3' end of the cDNA, respectively, in order to detect not only members of a gene family, but potentially any transcript.

In this modification it is preferred to remove the cap structure from the mRNA and subsequently to ligate an RNA oligonucleotide to the 5 end of the mRNA in a single-strand ligation. Said RNA oligonucleotide for example may have a length of 20–30 bases and preferably bears a recognition site for the restriction enzyme(s) used to cleave the double stranded cDNAs. After the restriction step is completed and the ligation of the double stranded linker molecules is completed, a linker primer and, instead of the primer directed against a gene family-specific domain, a primer derived from the sequence of the cDNA primer or from the sequence of the said RNA oligonucleotide is then used for reamplification.

Such a method for the general analysis of the expression of genes preferably comprises the steps:

(a) isolation of mRNA molecules from one or several samples to be analysed,
   (aa) attachment of an anchor sequence to the 5 end of the mRNA molecules, (b) synthesis of cDNA first strand molecules from the mRNA molecules, (c) amplification of the cDNA first strand molecules and labelling the amplification products, (d) transcript-specific shortening of the amplification products by cleaving with one or several restriction endonucleases, (g) separation of the amplification products according to their length, (h) analysing the separated amplification products.

Alternatively a further preferred method for the general analysis of the expression of genes is provided characterized by the steps:

(a) isolation of mRNA molecules from one or several samples,
   (aa) attachment of an anchor sequence at the 5' end of the mRNA molecules, (b) synthesis of cDNA first strand molecules from the mRNA molecules, (c) amplification of the cDNA first strand molecules, (d) transcript-specific shortening of the amplification products by cleavage with one or several restriction endonucleases, (e) attachment of linker molecules to the ends of the restriction fragments, (f) reamplification and labelling of the restriction fragments in which a primer directed against the linker molecule attached in step (e) and (i) a primer directed against the anchor sequence attached in step (aa) or (ii) a primer directed against the cDNA primer sequence used in step (b) are used,
   (ff) optionally a second reamplification and labelling in which "nested" primers are used,
      (fff) optionally a subtractive hybridization of two pools of amplification products which are to be compared with one another, (g) separation of the amplification products according to their length and, (h) analysis of the separated amplification products.

Step (a) of the method according to the invention comprises the isolation of mRNA molecules from samples to be analysed e.g. tissue samples which can be derived from animals, plants or microorganisms. Preferably one starts with several, i.e. at least two, tissue samples in order to carry out a differential analysis of gene expression from the different tissue samples. The isolation of the mRNA can be carried out according to known processes (cf. e.g. Sambrook et al., Molecular cloning: A Laboratory Manual, 2. Edition (1989), Cold Spring Harbor Laboratory Press, in particular chapter 7).

Step (aa) comprises the attachment of a selected anchor sequence to the 5' end of the RNA molecules. This anchor sequence preferably comprises an RNA oligonucleotide and can be attached to the mRNA molecules by decapping the mRNA and subsequent single-strand ligation by means of T4 RNA ligase. In this process it is also possible to use a suitably modified oligonucleotide which specifically hybridizes to the cap structure and causes an incorporation of the sequence complimentary to its own sequence in the reverse transcription step. The anchor sequence preferably contains a cleavage site for a restriction enzyme which is to be used later in order to ensure the detection of each transcript even when an internal cleavage site is absent.

Step (b) of the method according to the invention comprises the synthesis of single-strand cDNA molecules from mRNA. For this an oligo dT primer is preferably hybridized to the poly(A) tail of the mRNA and extended by means of a suitable enzyme such as reverse transcriptase or Tth polymerase. The oligo-dT primer can have extensions at the 5' end or/and at the 3' end. The extension at the 5' end can for example be an arbitrary sequence with preferably 20 to 30 nucleotides e.g. 24 nucleotides. The extension at the 3' end can be a sequence of 1 or several nucleotides, preferably 1 to 3 nucleotides e.g. 1 or 2 nucleotides. Instead of an oligo-dT primer it is also possible to use random primers for the cDNA synthesis which are preferably very short e.g. 6 to 10 nucleotides in length or have a high degree of degeneracy in order to statistically bind sufficiently frequently to the mRNA or oligonucleotides directed against a known sequence e.g. a gene family-specific domain can be used.

Step (c) of the method according to the invention comprises the synthesis of the cDNA second strand. In the method variant for analysing the expression of members of a gene family a selective amplification of the cDNA molecules of members of the selected gene family is carried out. This amplification is preferably carried out by means of PCR or other isothermal or non-isothermal amplification processes in which a gene family-specific primer is used which can hybridize with a "family-specific" domain conserved within the respective gene family. The gene family-specific primer can be degenerate or contain unspecifically-hybridizing bases such as inosine and has a length of at least five nucleotides preferably of at least 15 nucleotides. An oligonucleotide derived from the sequence of the cDNA primer can be used as a second primer or reverse primer. The reverse primer is preferably derived from the sequence of a 5' extension of the oligo-dT primer (cf. Frohman et al., Proc. Natl. Acad. Sci. USA 85 (1988), 8998–9002). On the other hand an oligonucleotide can also be used as the reverse primer which binds to a known RNA sequence e.g. a further gene family-specific primer.

In combination with step (c) it is also possible to carry out a labelling of the amplification products. For this one or both of the primers used can be labelled or the labelling can be carried out by using labelled nucleotides. Radioactive marker groups such as $^{32}P$, $^{33}P$ or $^{35}S$ as well as fluorescent dyes, biotin or antigens e.g. digoxigenin are on the one hand suitable for labelling. The labelling can also be carried out in a separate primer extension step ("linear PCR") using the amplification or reamplification products as a template.

In the method variant for general gene expression analysis there is no selective amplification but rather an amplification of all cDNA first strand molecules that are present. For this a primer directed against the anchor sequence attached in step (aa) is preferably used. A primer derived from the sequence of the cDNA primer used in step (b) e.g. a primer directed against a 5' extension of the cDNA primer is preferably used as the reverse primer. A first round of amplification is carried out using this primer combination with several e.g. ten amplification cycles preferably under "long range-PCR" conditions.

Step (d) of the method according to the invention comprises the transcript-specific shortening of the amplification products by cleavage with one or several restriction enzymes. A restriction enzyme or a combination of restriction enzymes is preferably used which cleaves the amplification product with a statistically high probability, restriction enzymes with a four-base recognition sequence such as Mse I, Hinf I or Sau3A I are preferably used.

If it is intended to recover the PCR products, double-stranded linker or adapter molecules are ligated as step (e) to the ends of the restriction fragments produced in step (d). Linker molecules with different ends are preferably used, in which one end of the linker matches the ends of the restriction fragments produced by the restriction enzyme whereas the other end is designed such that no ligation (neither self nor foreign ligation) is possible for example by a suitable single-stranded overhang. In addition the ends of the restriction fragments can be adapted to the ends of the respectively used linker molecules by subsequent modification e.g. by filling in the overhanging ends.

Step (f) of the method according to the invention comprises the reamplification and—provided it has not yet occurred—labelling of the restriction fragments. For this a primer combination is preferably used comprising (i) a primer directed against the linker molecule and (ii) a primer directed against the sequence of the anchor oligonucleotide attached to the 5' end of the mRNA in step (aa) or a primer directed against the sequence of the cDNA primer used in step (b). In the case of a gene family-specific expression analysis, a primer combination is preferably used comprising (i) a gene family-specific primer and (ii) a primer directed against the linker molecule, against the anchor oligonucleotide or the sequence of the cDNA primer. All primers used can be identical with the primers used previously in step (c) or have an extension of one or several additional bases at their 3' end. Gene family-specific primers can in addition be directed against a site located further within the respective amplification product within the family-specific domain. The labelling of the reamplification products is carried out as described in step (c).

If fluorescent-labelled primers are used, the fluorescent colour can be used to code the respective primer; for example the last base of a primer extended by one base at its 3' end can be labelled by one of several e.g. four colours. If biotin-labelled primers are used in step (c), the amplification products can be purified before the reamplification by binding to streptavidin-coated magnetic particles or streptavidin-coated reaction vessels.

In order to enable a subdivision of the ca. 15000 different PCR products obtained in this step (when using family-unspecific primers) the PCR primers preferably carry an extension at their 3' end. A two-base extension on the linker primer is for example suitable enabling 16 different combinations and a one-base extension on the reverse primer (A, C or G three different combinations being possible) so that 3×16=48 amplification reactions with different primer combinations have to be carried out for each sample to be examined. In addition, as an alternative to this "3' preparation", the amplification can be carried out at the 5' end by combining the linker primer and a primer directed against the anchor sequence. This method variant has the advantage that a primer containing an oligo(dT) sequence is not necessary.

The optional step (ff) of the method according to the invention comprises a reamplification of the amplification products obtained in step (f) using "nested" primers i.e. using primers that are extended at their 3' end by one or more bases compared to the primers used in step (f). This renewed reamplification enables the rare amplification products present in a low concentration to be amplified to a detectable concentration and subsequently detected (McClelland and Welsh (1994), PCR Methods Appl. 4, 66–81; Ralph et al. (1993), Proc. Natl. Acad. Sci. USA 90, 10710–10714).

The optional step (fff) of the method according to the invention comprises a subtractive hybridization of two amplification product pools to be compared in order to subsequently only examine those products by gel electrophoresis whose frequency differs between the two pools. These products then represent differentially expressed genes in the two initial samples and are therefore of particular interest, whereas in many cases it is not necessary to have information about non-differentially expressed genes. The method of subtractive hybridization is described for example by Bautz and Reilly (1966), Science 151, 328–330 and Zimmermann et al. (1980), Cell 21, 709–715. In order to carry out such a subtractive hybridization one of the pools of amplification products to be compared (driver) can be labelled e.g. biotinylated e.g. by using biotinylated primers and then hybridized with a deficiency of the other pool (tester). Subsequently the labelled hybridization products can, for example in the case of a biotin label, be separated by binding to streptavidin-coated magnetic particles (cf. e.g. Wang and Brown (1991), Proc. Natl. Acad. Sci. USA 88, 11505–11509). If necessary this subtraction step can also be carried out several times in succession. The amplification products remaining in solution can then be subjected again to an amplification in order to have adequate amounts of DNA available for the subsequent detection. If such an amplification is carried out after the subtraction, then a suitable marker group for the detection is preferably not introduced until this step. In this manner it is for example possible to distinguish between a biotin label for separating hybrids after the subtraction and a label to visualize fragments.

This variant of the method according to the invention can be applied to the detection of "yes" or "no" expression states (higher excess of labelled DNA, fewer hybridization cycles) as well as to the detection of up or down regulation of genes (lower excess of labelled DNA, more hybridization cycles) (Fargnoli et al. (1990), Analyt. Biochem. 187, 364–373).

Optionally the subtraction can also be followed by a normalization i.e. a levelling of the various concentrations of the individual amplification products. This normalization ensures that in the subsequent step (h), the analysis of the separated amplification products, amplification products representing rare transcripts that are present in low concentrations are also detected. Such a normalization can be carried out before, after or during the amplification that follows the subtraction. A suitable method for normalization is for example described by Ko (1990) Nucleic Acids Res. 19, 5705–5711.

Step (g) of the method according to the invention comprises the separation of the amplification and reamplification products according to their length in a suitable system e.g. electrophoretically or by HPLC. An electrophoresis in a denaturing or non-denaturing polyacrylamide gel is particularly preferred. This separation can be carried out with a single reaction mixture or concurrently with several reaction mixtures that are to be compared with one another. The visualization of the separated products is carried out according to the introduced marker group e.g. by autoradiography, chemiluminescence or specific detection of labelled molecules by staining or irradiation with UV light. The products can be detected in the gel (untreated or fixed and dried) or after transfer to a suitable support preferably a hybridization membrane.

The method of direct blotting electrophoresis is particularly suitable for such a transfer. The detection can also be carried out by unspecific DNA staining using silver compounds or suitable dyes (e.g. SYBR Green I) or by hybridizing the membrane carrying the products with a suitable probe. If fluorescent groups are used for labelling, the separation and detection can be carried out by means of an automated sequencing apparatus or/and the detection can be carried out by means of a fluorescent gel scanner or fluorimager.

Step (h) comprises the analysis of the separated amplification and reamplification products. In this process bands of interest can be isolated and amplified again. In the case of a renewed amplification the same primers as in the reamplification according to step (f) can be used. The bands can for example be isolated by using a scalpel to cut them out of the gel or from the support onto which the separated products were transferred. The excised bands can be subsequently incubated in a PCR mixture for reamplification. The products obtained in this process can be used for direct sequencing without a cloning step. The cycle sequencing method is particularly suitable for this. The previously used PCR primers can be used as sequencing primers. Alternatively primers extended at their 3' end can be used for reamplification or/and sequencing in order to get rid of possible impurities of a band caused by other amplification products. The necessary 3' extension of the primers used for this purpose can be determined if the bands are detected by means of fluorescent-labelled primers and if mixtures of different fluorescent-labelled primers have been used in step (f) or (ff) whose last base or bases are coded by their respective label.

Before being used for sequencing, the reamplification products can be checked for purity preferably by another electrophoresis in a denaturing polyacrylamide gel. If amplification products occur whose size differs from the desired amplification product, then it is possible to carry out a further purification by again cutting out the desired bands and subsequent reamplification. The reamplification products can additionally also be used in Southern, Northern or in situ hybridization experiments. In addition they can— provided they have a still unknown nucleic acid sequence— be used to isolate matching genomic or cDNA clones from appropriate libraries.

If the number of different products that are obtained in an amplification reaction is small enough then individual products can be reamplified directly from the total reaction by using suitable selective primers which for example have an extension of at least one base at their 3' end compared to the previously used primers. Such a situation would occur in particular if, according to step (fff), a subtraction has been carried out in several parallel mixtures. Each subtraction reaction would then only contain a few for example 5–10 different amplification products. In order to selectively isolate each of these individually by amplification from the subtraction reaction, knowledge about some of the bases bordering on the amplification primers used previously is helpful. This information can for example be obtained by using mixtures of four primers in each case for the amplification carried out after the subtraction wherein these primers are extended at their 3' end by one of the four possible bases and carry a fluorescent label whose colour unequivocally codes the respective last base of a primer. If the amplification products are now separated and examined in UV light, the fluorescent colour of a band enables deductions to be made about the primer incorporated into the corresponding product which can then be used subsequently for selective reamplification. In order to obtain an adequate number of coding possibilities (for example $4^1$, $4^2$=16, $4^3$=64 etc.) suitable fluorescent coded primers can be combined in each case with unlabelled reverse primers in several parallel mixtures and used for amplification.

In addition a number of modifications to the method according to the invention are conceivable. Thus in step (b) the first strand cDNA can for example be provided at its 3' end with a specific nucleic acid sequence and, in addition to the gene family-specific primer, an oligonucleotide directed against this specific nucleic acid sequence can be used as a reverse primer in the subsequent amplification in step (c).

The specific nucleic acid sequence for example comprises a homopolymer or an arbitrary sequence with a length of preferably 20 to 30 nucleotides.

A further modification of the method according to the invention can for example comprise converting the first strand cDNA into oligomeric or/and circular molecules by self ligation e.g. in a ligation reaction with RNA ligase and using a downstream directed oligonucleotide which optionally has an extension at its 3' end of preferably 1 to 3 nucleotides and is at least partially complementary to the cDNA primer as a reverse primer in addition to the gene family-specific primer for the subsequent amplification in step (c).

Yet a further modification of the method according to the invention is to already carry out the restriction cleavage in step (d) without prior amplification on double-stranded cDNA. This procedure enables loss of very long transcripts of several kb in length to be avoided which could be lost during an amplification of the complete first strand cDNA.

In addition it is preferred that in the method according to the invention and in the modifications of this method discussed further below, the oligonucleotide primers used have a length of preferably at least 15 nucleotides, particularly preferably of at least 18 nucleotides in order to improve the reproducibility of the band pattern obtained. In addition the oligonucleotide primers can also be replaced by synthetic nucleic acid analogues or derivatives, e.g. by peptidic nucleic acids (PNA), provided that they have a 3'—OH group at their 3' end that is accepted by the polymerase.

Moreover the oligonucleotides used in the method according to the invention and in modifications thereof i.e. anchor oligonucleotides, cDNA primers, amplification primers etc. can contain one or several recognition or cleavage sites for restriction enzymes. In this manner the loss of amplification products that are not cleaved by the restriction enzyme can be avoided if no filling in of the ends is carried out before the linker ligation.

The method according to the invention has surprising advantages compared to the known differential display technique since in this case perfectly matching primers with an optimal length for the amplification reactions are used. This leads to a higher reproducibility of the method. In contrast only an inadequate reproducibility is achieved with the DD experiments of the state of the art with the often very short primers used there and with toleration of mismatches of binding primers (Bertioli et al., Supra) since the method is extremely dependent on certain method parameters e.g. the annealing temperature during the PCR. A consequence of this poor reproducibility observed in DDRT experiments is that at least one or two replicate experiments have to be carried out per reaction in order to detect artefacts as such. Together with the high number of different primer combinations that are necessary to detect at least a majority of all the transcripts with a certain probability (Bauer et al., Supra), the procedure for the DDRT of the state of the art is extremely laborious. Nevertheless in this method, due to the statistical binding properties of arbitrary primers, there is no defined number of primer combinations which could guarantee the detection of all transcripts. In contrast in the method according to the invention replicate experiments are superfluous and the number of primer combinations required for a complete examination can be easily calculated from the expected number of transcripts in an examined tissue (for example 15000) and the number of products which are to be allowed in a single amplification reaction (for example 100). In this process the detection of each transcript can be ensured by the fact that the oligonucleotides used as cDNA primers or as anchors contain cleavage sites for the restriction enzyme used in step (d). Moreover the omission of replicate reactions enables 30 or more different RNA samples to be examined on a single gel.

A further advantage of the method according to the invention over the DD technique is that the differential expression of all examined bands can be confirmed by Northern experiments. In contrast in the case of DD experiments of the state of the art only five of a total of 15 bands obtained could for example be confirmed as being differentially expressed while four gave a false positive signal and a further six gave no signal at all in the Northern blot (cf. Liang et al, Supra).

In addition the method according to the invention excludes the multiple detection of a transcript. This is a result of the fact that, if non-phosphorylated oligonucleotides are used for the linker preparation, an amplification can only occur between a defined region of a transcript (its 3' end, its 5' end or a family-specific domain) and a linker but never between two ligated linkers. In contrast in DDRT experiments of the state of the art a given transcript can be recognized by different primer combinations and in this way be multiply detected. Thus for example one and the same transcript was represented by 15 different DDRT bands which has been generated by combination of different 5' primers with different 3' primers (Linskens et al. (1995), Nucleic Acids Res. 23, 3244–3251).

Moreover the products obtained in the method according to the invention can be sequenced directly after the reamplification in a simple manner without requiring a cloning step. This sequencing is preferably carried out by the cycle sequencing technique. This technique is unsuitable for the primers used in DD experiments with a length of about 10 nucleotides. Moreover DDRT products of the state of the art are often flanked by two molecules of the same primer which excludes the use of the respective amplification primer as the sequencing primer (Guimaraes et al. (1995), Nucleic Acids Res. 23, 1832–1833).

A further advantage of the method according to the invention is a major reduction in the number of individual reactions that have to be carried out as well as in the amplification products that have to be examined provided a subtractive hybridization is carried out in step (fff). Whereas several hundred PCR preparations are necessary to carry out DD experiments of the state of the art which are subsequently separated in several hundred polyacrylamide gel lanes (Liang and Pardee, Supra; Bauer et al., Supra), it is possible in the method according to the invention to subdivide the cDNA pools generated in step (b) into several, for example eight or 12, subpools by using primers in step (f) which are extended at their 3' end by one or two bases in each case compared to the sequence of their common binding site. Subpools which correspond to one another are then subtracted in parallel and the products of each subtraction are analysed in its own gel lane.

Compared to the known method of "cDNA-RDA" (Representational Difference Analysis of cDNA; Hubank and Schatz (1994), Nucleic Acids Res. 22, 5640–5648) the method according to the invention has several advantages: firstly each transcript is represented here by exactly one amplification product which avoids the undesired loss of some transcripts as well as the multiple detection of one and the same transcript, secondly the reduced complexity of the hybridization reactions compared to cDNA-RDA as well as compared to the subtractive hybridization of complete cDNA molecules leads to more complete and more rapid reaction courses (Sargent (1987), Methods in Enzymol. 152, 423–432) and thirdly the steps provided within the scope of the method according to the invention allow the specific detection of rare transcripts.

In addition the sequencing of DD products is often impeded by the simultaneous presence of contaminating cDNA molecules of the same size. For this reason a complicated purification procedure for DD products is necessary for further analysis (Liang et Pardee, Supra; Bauer et al. Supra; Li et al (1994), Nucleic Acids Res. 22, 1764–1765).

In contrast to the DD method of the state of the art, the method according to the invention additionally allows an at least semi-quantitative analysis of the results with regard to the signal strength of a given transcript. This is demonstrated by comparing the method according to the invention with Northern hybridizations carried out as a control.

A further advantage of using the method according to the invention for expression analysis of gene families is that the resulting products generally contain a part of a family-specific domain as well as a flanking sequence which enables a classification and identification of the cDNA molecules obtained. In contrast 3' untranslated regions are usually preferably obtained in the case of the DD technique which yield sequence information of only very limited value.

Due to its sensitivity the method according to the invention can also be used to analyse transcripts of interest from a few or even individual cells. Thus this technique can for example be used in developmental biology to isolate new genes, to identify new members of gene families of interest, to exactly define different life stages of an organism and to examine the life cycle of a cell and thus also to examine deviations from the normal life cycle e.g. in cancer research.

The present invention in addition concerns modifications of the method described above. One of these modifications is that in the embodiment for general expression analysis the cDNA second strand synthesis is carried out in another conventional manner. For example the tendency of single-stranded cDNA to form terminal hairpin loops can be utilized or a specific nucleic acid sequence, for example a homopolymer or a single-stranded oligonucleotide, can be attached to the first strand cDNA in order to provide a primer binding site for the second strand synthesis (see for example Sambrook et al., Supra, in particular chapter 8; Troutt et al. (1992), Proc. Natl. Acad. Sci. USA 89, 9823–9825).

Yet a further modification of the described methods is that the first strand cDNA is provided with a specific nucleic acid sequence as described above and in the amplification in step (c) an oligonucleotide directed against the attached specific nucleic acid is used as the first primer instead of the gene family-specific primer and an oligonucleotide derived from the sequence of the cDNA primer is used as the reverse primer. The reverse primer can optionally have a 3' extension. The specific nucleic acid sequence can comprise a homopolymer or an arbitrary sequence The specific nucleic acid sequence is preferably ligated to the first strand cDNA preferably by ligation e.g. by means of RNA ligase. It can be modified at its 3' end (e.g. by introducing an amino group) in order to prevent ligation of more than one oligonucleotide molecule to the cDNA.

In yet a further modification of the method according to the invention the first strand cDNA is converted into oligomeric or/and circular molecules by self ligation e.g. with RNA ligase and in the subsequent amplification in step (c) two oligonucleotides directed against the cDNA primer are used as primers one of which is directed upstream and the other downstream. The reamplification after the restriction and ligation step can be carried out with the upstream or/and with the downstream primer in addition to the primer directed against the linker. Each of the two primers can have an extension at its 3' end i.e. be extended by one or several bases. The upstream and downstream primers are preferably selected such that they do not overlap or only to a slight extent in order to avoid a hybridization of both primers during the amplification.

Compared to known methods for the differential expression analysis of genes based on subtractive hybridization, the method according to the invention is distinguished by an improved reproducibility and can therefore be used routinely. This improved reproducibility is based on the fact that in the state of the art cDNA molecules have been used with a length of often up to several thousand bp and moreover complete mRNA or cDNA pools have been used. These problems do not occur when subtractive hybridization is used to analyse amplification products which have been obtained by the method according to the invention. These amplification products are substantially shortened compared to the cDNA molecules of the state of the art and, due to the design of the primers (e.g. the selection of different 3' extensions for otherwise identical primers), a pool of amplification products can be easily subdivided into several e.g. 8, 12 or 16 subpools. Subpools which correspond to one another can then be subtracted in parallel.

Yet a further subject matter of the invention is a reagent kit to analyse the expression of genes especially for use in a method according to the invention. This reagent kit comprises preferably in a spatially separate arrangement:

(a) an enzyme for the cDNA first strand synthesis, (b) at least one enzyme for the synthesis of cDNA second strands and for the amplification of DNA fragments, (c) optionally at least one restriction enzyme, (d) optionally at least one double-stranded DNA linker molecule and an agent for attaching the linker molecule to DNA fragments, (e) optionally at least one single-stranded RNA oligonucleotide and an agent for attaching the RNA oligonucleotide to the 5' end of mRNA molecules, (f) single-stranded nucleic acid primer molecules selected from the group comprising (i) at least one gene family-specific primer, (ii) at least one oligo-dT nucleotide, (iii) at least one primer derived from the sequence of the DNA linker molecule, (iv) a primer derived from the sequence of the RNA oligonucleotide,. (v) a set of random primers, (vi) primers according to (i–v) with a 3' extension or/and 5' extension, (vii) primers according to (i–vi) which carry marker groups and (viii) primers according to (vii) which contain a 3' extension coded by the type of label e.g. the colour of a fluorescent label, (g) agent for labelling and for detecting nucleic acids and (h) optionally further reagents such as RNase inhibitor, nucleotides, buffers, streptavidin-coated reaction vessels or magnetic particles.

Individual reagents of the kit can if necessary be obtained separately. In addition to the reagents the kit can also contain suitable buffers for the enzymes used in each case.

It is indended to further elucidate the present invention by the following figures, sequence protocols and examples.

FIG. 6 shows the allocation of the genes identified by the method according to the invention to MADS box gene families.

Figure 1:
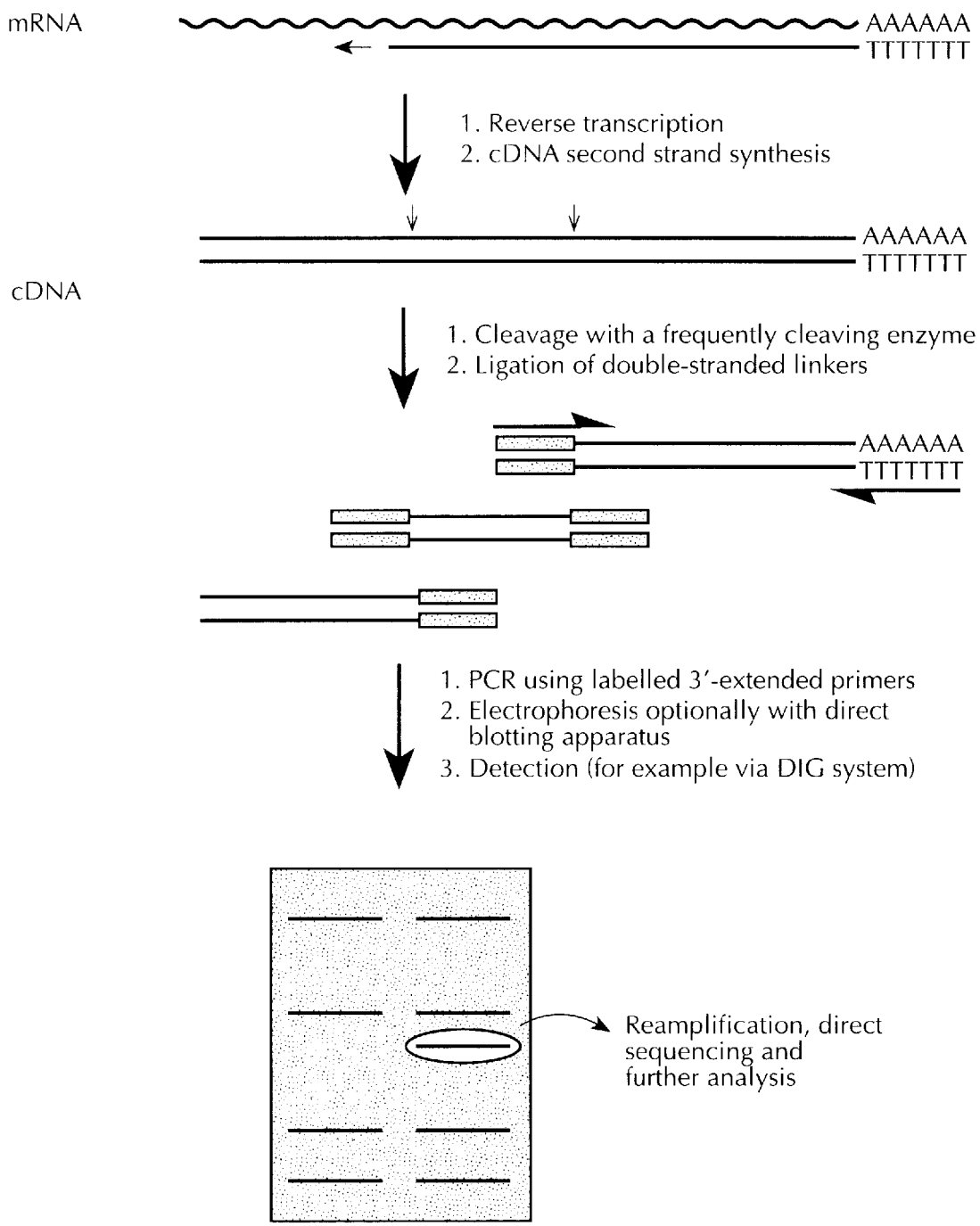
FIG. 1 shows a schematic representation of an embodiment of the method according to the invention for the general expression analysis of genes.
Figure 2:
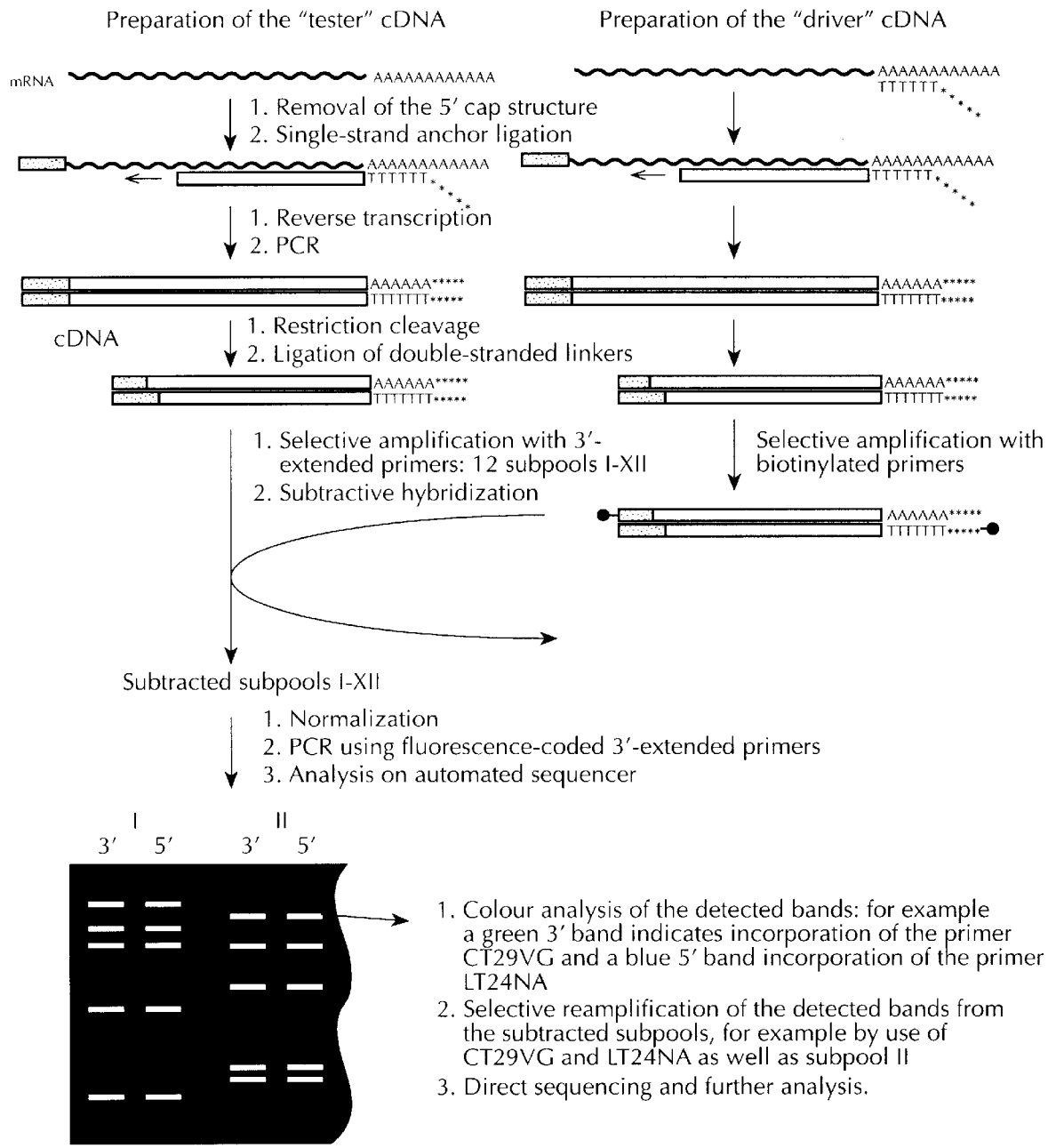
FIG. 2 shows a schematic representation of a further embodiment of the method according to the invention for the general expression analysis of genes including a subtraction step and the use of fluorescent-coded primers for reamplification.

SEQ ID No. 1 shows the sequence of an RNA oligonucleotide,

SEQ ID No. 2 shows the sequence of the primer CT29V,

SEQ ID No. 3 shows the sequence of the primer AP23,

SEQ ID No. 4 shows the sequence of the primer LT20,

SEQ ID No. 5 shows the sequence of the primer LT24,

SEQ ID No. 6 shows the sequence of the primer P038,

SEQ ID No. 7 shows the sequence of the primer P041,

SEQ ID No. 8 shows the sequence of the primer P042,

SEQ ID No. 9 shows the sequence of the primer P043,

SEQ ID No. 10 shows the sequence of the primer LR32,

SEQ ID No. 11 shows the sequence of the primer BLT18,

SEQ ID No. 12 shows the sequence of the primer P046,

SEQ ID No. 13 shows the sequence of the primer P009 and

SEQ ID No. 14 shows the MADS domain consensus sequence.

EXAMPLE 1

Isolation of RNA

Indian maize plants (*Zea mays* ssp. *mays*), inbred line T232 and teosinte plants (*Zea mays* ssp. *parviglumis*) Central Balsas breed were cultured for 7–8 weeks in a greenhouse. At this time point the plants exhibited the developmental stages I and J defined by Cheng et al. (Am. J. Bot. 70 (1983), 450–462).

Male and female inflorescences were harvested, frozen in liquid nitrogen and used to isolate the total RNA according to the guanidinium chloride isolation method of Sambrook et al (Molecular Cloning: A Laboratory Manual, 2nd Edition (1989), Cold Spring Harbor Laboratory Press).

The quality of RNA preparations was tested by Northern hybridization (Sambrook et al, Supra) using a maize glyceraldehyde-3-phosphatedehydrogenase (GAPDH) probe. In order to remove genomic DNA 50 $\mu$g total RNA was incubated for 15 min at 37° C. with 1 $\mu$l of the RNase inhibitor RNasin (Promega, 40 U/$\mu$l) and 5 $\mu$l RQ1 RNase-free DNase (Promega, 1 U/$\mu$l) in 100 $\mu$l reverse transcriptase (RT) buffer (Frohman et al., Proc. Natl. Acad. Sci. USA 85 (1988), 8998–9002). The samples were extracted with phenol saturated with Tris/EDTA (TE) and with chloroform/isoamyl alcohol (24:1) and precipitated with ethanol. After centrifugation for 30 min. at 20000× g and 0° C. the total RNA was dissolved in 1 mM EDTA (pH 7.5). The poly(A)+ mRNA was isolated using oligo(dT) Dynabeads (Dynal, Oslo).

EXAMPLE 2

Analysis of Sex-Dependent Gene Expression

The total RNA isolated from male and female maize inflorescences was firstly dephosphorylated. For this 50 $\mu$g precipitated RNA was dissolved in a mixture of 40 $\mu$l water treated with diethyl pyrocarbonate ("DEPC water"), 5 $\mu$l 10× AP buffer (Boehringer Mannheim), 1 $\mu$l 50 mM dithiothreitol and 1.5 $\mu$l RNasin (Promega). After addition of 4 $\mu$l alkaline phosphatase (AP; 1 U/$\mu$l; Boehringer Mannheim) it was incubated for 1 hour at 37° C. In order to inactivate the phosphatase 1 $\mu$g proteinase K (Boehringer Mannheim) was added and it was incubated for 1 hour at 37° C. The samples were extracted as described above with TE-saturated phenol and with chloroform/isoamyl alcohol and precipitated with ethanol. The precipitates were each dissolved in 40 $\mu$l DEPC water.

After addition of 5 $\mu$l 10× TAP buffer, 1.25 $\mu$l RNasin, 1 $\mu$l 100 mM ATP and 3 $\mu$l acid pyrophosphatase from tobacco (TAP; 5 U/$\mu$l; Epicentre) it was incubated for 1 hour at 37° C. in order to effect a decapping. The reaction mixtures were firstly extracted with phenol, then extracted with chloroform/isoamyl alcohol and precipitated with ethanol. Subsequently the RNA was dissolved in 100 $\mu$l elution buffer (Dynal) and the poly(A)+ mRNA was isolated using oligo(dT) Dynabeads (Dynal).

After elution in 4.2 $\mu$l water it was admixed with 1.8 $\mu$l ligation mix (prepared from 3 $\mu$l 10× RNA ligase buffer [Boehringer Mannheim], 0.75 $\mu$l RNasin, 1.5 $\mu$l 2 mM ATP, 1.5 $\mu$l T4-RNA ligase [10 U/$\mu$l; Boehringer Mannheim] and 1 $\mu$g anchor-RNA oligonucleotide 5'-CAC GAU CUG AGG CCG AUC GAU UCA-3' in 1 $\mu$l H$_2$O) and ligated for 20 hours at 16° C. The ligation preparation was precipitated with ethanol and the precipitate was taken up in 2.8 $\mu$l DEPC water.

1.5 $\mu$l of a mixture of 4.3 $\mu$l 5× RT buffer (Boehringer Mannheim), 1 $\mu$l of a 20 mM solution of DATP, dTTP, dGTP and dCTP, 1 $\mu$l cDNA primer CT29V (30 pmol/$\mu$l; 5' -ACC TAC GTG CAG AT$_{15}$V-3' in which V=G, A or C) and 1 $\mu$l M-MuL V reverse transcriptase (20 U/$\mu$l; Boehringer Mannheim) were added for reverse transcription and it was incubated for 1 hour at 37° C. and subsequently for 30 min. at 42° C. The reactions were filled to 20 $\mu$l with TE buffer.

2 $\mu$l in each case of the anchor-cDNA pool obtained in this way was admixed on ice with 28.5 $\mu$l H$_2$O, 5 $\mu$l 10× PCR buffer (670 mM Tris/HCl, pH 8.8; 170 mM (NH$_4$)$_2$SO$_4$; 1% Tween 20), 5 $\mu$l of a 1 mM solution of DATP, dTTP, dGTP and dCTP, 8 $\mu$l 10 mM MgCl$_2$, 0.1 pmol of each primer CT29V and AP23 (5'-CAC GAT CTG AGG CCG ATC GAT TC-3') in 1 A$\mu$H$_2$O and 0.5 $\mu$l Taq DNA polymerase (5 U/$\mu$l; Boehringer Mannheim) for the cDNA second strand synthesis and amplification. The reactions were overlayered with paraffin oil and placed in a Trioblock thermocycler (Biometra) preheated to 95° C. After initial denaturation for 5 min at 95° C., 20 cycles of the following amplification programme were carried out: 30 sec. denaturation at 95° C., 2 min. annealing and extension at 72° C. The reactions were purified on QiaQuick columns (Quiagen); the elution was carried out with 20 $\mu$l TE. After addition of 2.3 $\mu$l 10× buffer A (Boehringer Mannheim) and 1 $\mu$l Sau3AI (4 U/$\mu$l; Boehringer Mannheim) it was cleaved for 1.5 hours at 37° C. The reactions were precipitated with ethanol.

1.5 nmol of each of the oligonucleotides LT20 (5'-TCA CAT GCT AAG TCT CGC GA-3') and LT24 (5'GAT CTC GCG AGA CTT AGC ATG TGA C-3') were mixed together in a volume of 50 $\mu$l H$_2$O and heated for 3 minutes to 90° C. The reaction mixture was adjusted to 50 mM Tris/HCl (pH 7.5) and 10 mM MgCl$_2$ and slowly cooled to 4° C. for the generation of double-stranded linkers.

The precipitated restriction fragments were taken up in 4 $\mu$l total volume of a ligation mixture according to Cobianchi and Wilson (Methods Enzymol. 152 (1987), 94–110) with addition of 0.5 $\mu$l of the linkers produced as described and ligated for 16 hours at 16° C. The unligated linkers were removed on QiaQuick columns.

A fifth of the purified ligation reaction was combined with 10 μl 10× PCR buffer, 16 μl 10 mM MgCl$_2$, 5 Ml 1 mM dATP, dTTP, dGTP and dCTP, 20 pmol each of CT29V and LT24 in a total volume of 100 μl for subsequent amplification. After heating for 5 min to 95° C. in a thermocycler 5 U Taq DNA polymerase was added and 20 cycles of an amplification were carried out under the following conditions: 30 sec. denaturation at 95° C., 90 sec. annealing and extension at 72° C.

In each case 1 μl amplification product was used for a second round of amplification. This was carried out in accordance with the above-mentioned conditions but in a total volume of 30 μl for 30 cycles and in each case using a combination of one of the digoxigenin-labelled primers DIG-CT29A (sequence identical to CT29V but with an "A" as the unequivocal last base instead of the degenerate last base "V"), DIG-CT29C or DIG-CT29G with one of the 16 possible primers LT24NN extended by two bases compared to LT24. In each case 3 μl of a reaction was admixed with 1.5 μl cycle sequencing stop solution from Promega.

Then preparations corresponding to one another of the tissues to be compared were loaded next to one another onto two lanes of a denaturing 3.5% polyacrylamide gel. DIG-labelled DNA molecular weight marker VIII (Boehringer Mannheim) was loaded onto a free lane as a length standard. The electrophoretic separation and transfer to a nylon membrane was carried out by means of a GATC 1500 sequencing apparatus (MWG Biotech) according to the manufacturer's instructions. The nylon membrane was treated in an unfixed state according to the manufacturer's instructions for the chemiluminescence detection of nucleic acids. After exposing X-ray film (Kodak X-Omat) the membrane and the film were brought into coincidence and bands which appeared differentially were cut out of the membrane by means of a scalpel. The respective pieces of the membrane were incubated in a 50 μl reamplification reaction under the above-mentioned conditions in which 30–40 cycles were used. The successful reamplification and the purity of the reamplification product were checked by means of agarose gel electrophoresis.

EXAMPLE 3

Analysis of Sex-Dependent MADS Box Gene Expression

The mRNA isolated in example 1 from male and female inflorescences was converted into single strand cDNA according to the RACE protocol (Frohman et al., Supra) to obtain cDNA pools. A PCR was carried out with the cDNA pools using the RACE adapter primer described by Frohman et al, Supra and a mixture of gene family-specific MADS box primers. All MADS box primers were directed towards gene family-specific sequences that code for derivatives of a highly conserved amino acid motif and comprise all variations known from plants. In order to achieve the highest possible specificity the degree of degeneracy was kept as low as possible. The primers used in this publication were as follows:

P038 (directed against the amino acid sequence "IKRIEN") 5'-GAT CAA G(A/C)G (G/C)AT CGA GAA-3'; P041 (against "MKRIEN"), 5'-GAT GAA G(A/C)G (G/C) AT CGA GAA-3'; P042 (against "IKHIEN"), 5'-GAT CAA GCA (C/T)AT CGA GAA-3'; P043 (against "IKKIEN"), 5'-GAT CAA GAA GAT CGA GAA-3'.

The amplification was carried out as follows using primer P038:

At first a 50 μl reaction mixture was pipetted together on ice which contained 67 mM Tris/HCl, pH 8.8; 17 mM (NH$_4$)$_2$SO$_4$; 0.1% Tween 20; 0.8 mM MgCl$_2$; 20 μM of each dNTP; 1.5 pmol of the primer P038 and 1 μl of the respective cDNA pool. After overlayering with paraffin oil the reaction mixtures were heated for 5 min to 95° C. in a Trioblock thermocycler (Biometra, Göbttingen). After cooling to 65° C., 2.5 U Taq DNA polymerase (Boehringer Mannheim) was added. 30 cycles of linear amplification were carried out using the following parameters: denaturation for 30 sec. at 95° C., annealing for 100 sec. at 54° C., extension for 2 min. at 72° C. Subsequently the reaction mixtures were cooled to 65° C.

For an exponential amplification 50 μl of a reaction mixture preheated to 65° C. which contained 100 μM dNTPs, 15 pmol RACE adapter primer and primer P038 and 2.5 U Taq DNA polymerase was added to the linear amplification reactions. Then a PCR was carried out using the above-mentioned parameters for 24 cycles, followed by a subsequent extension for 10 min at 72° C. The PCR products were purified on QiaQuick columns (Quiagen, Hilden). ⅕ (10 μl) of the eluate was incubated for 3 hours at 37° C. with 15 U of the restriction enzymes Mse I (New England Biolabs), Hinf I or Sau3AI (Boehringer Mannheim) in 50 μl of the respective restriction buffer. After a subsequent incubation for 10 min at 65° C., the nucleic acids were precipitated with ethanol and isolated by centrifugation (30 min, 20000g× at 4° C.). The residue was resuspended in 5 μl TE.

If desired, radioactive primer extension reactions can already be carried out at this stage as described below. On the other hand a linker ligation can be carried out for reamplification as described in the following. For this ½ μl of the resuspended restriction fragments Was incubated for 1 hour at 37° C. in 10 μl filling in mixtures (50 mM Tris/HCL, pH 8.0; 6 mM MgCl$_2$; 10 mM dithioerythritol; 100 μM of each dNTP; 40 μg bovine serum albumin per ml; 0.5 U T4-DNA polymerase (Boehringer Mannheim)). The fragments were then precipitated with ethanol and isolated as described above. The pellets were resuspended in 2 μl TE buffer. Double-stranded linkers were prepared from 1.25 nmol of each of the oligonucleotides LR32 (5'-ACT CGA TTC TCA ACC CGA AAG TAT AGA TCC CA-3') and BTL18 (5'-TGG GAT CTA TAC TTT CAA-3') as described in example 2. The linkers were ligated as described in example 2 to the restriction fragments that had been filled in at their ends; in this process in each case 0.5 μl of the linkers and 2 μl resuspended end filling-up reaction were incubated in 4 μl ligation buffer. The unligated linkers were removed on QuiaQuick columns.

Then a reamplification was carried out under the above-mentioned PCR conditions using 5 μl purified ligation mixture as a template in a total of 15 cycles. The respective MADS box primers (e.g. P038) were labelled with $^{32}$P according to the instructions enclosed with the "fmol DNA sequencing system" (Promega). Then half a microliter of the reamplification products was used to prepare a 10 μl primer extension mixture which contained 50 μM dNTPs, 1 U Taq DNA polymerase and 0.4 μl labelled MADS box primers. The reaction mixtures were placed in the wells of a preheated (95° C.) thermocycler and initially denatured for 3 min. at 95° C., followed by a programme of 30 sec. at 95° C., 30 sec. at 54° C. and 1 min at 72° C. for 30 cycles. After the final extension, 5 μl of the cycle sequencing stop solution from Promega was added. A "Sequamark" 10 bp ladder (Research Genetics, Huntsville, Ala.) was prepared as a length standard. For the gel electrophoretic analysis the extension mixture was heated for 2 min to 70° C. and 2 μl was applied to a denaturing 5% acrylamide gel. The gels were allowed to run for 3 hours at 45 W, fixed in 5% acetic acid/10% ethanol and dried in air. Then the gels were exposed for 4–12 hours on a Kodak X-Omat X-ray film.

Figure 3:
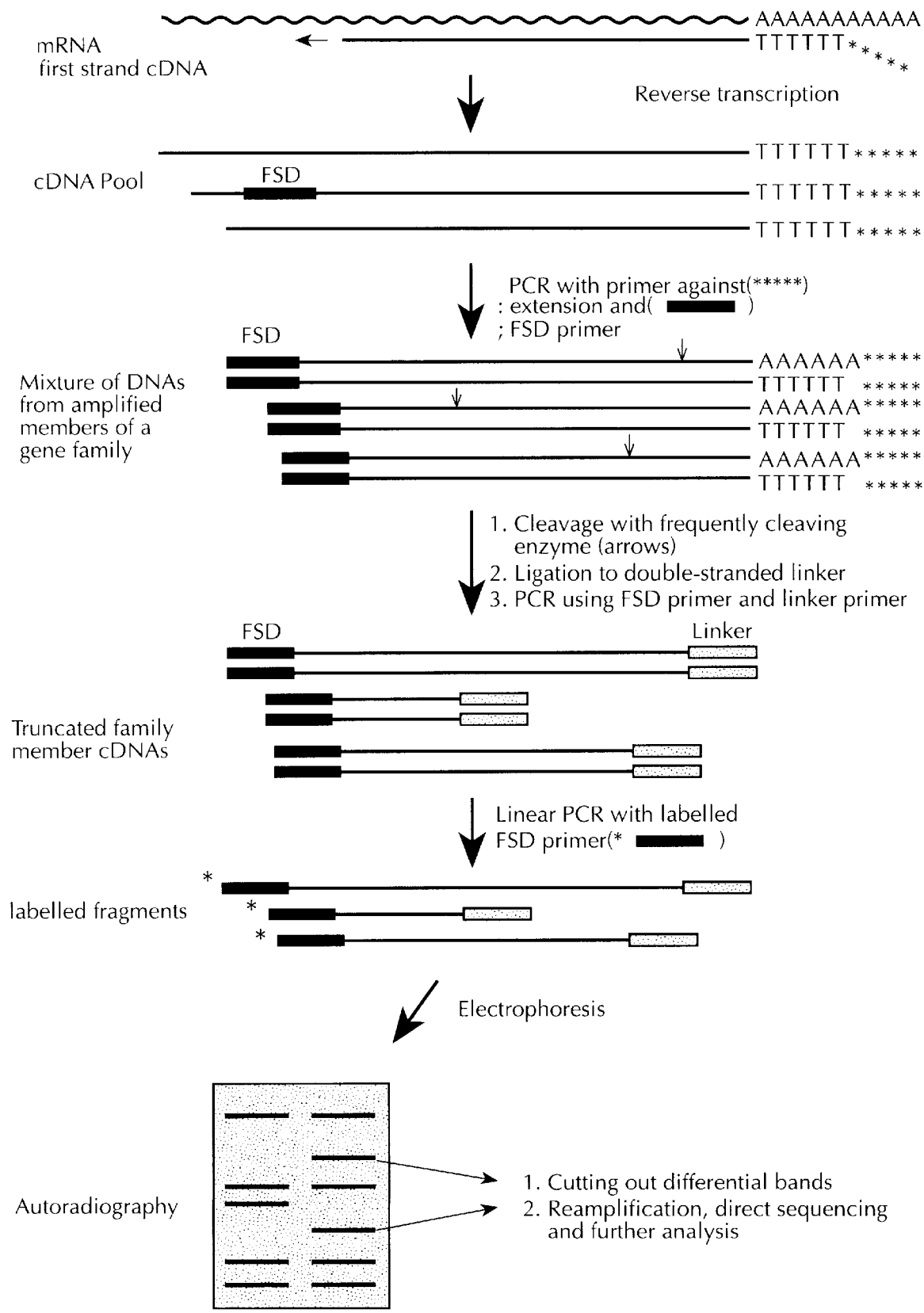
FIG. 3 shows a schematic representation of a further embodiment of the method according to the invention for the expression analysis of gene families.
Figure 4:
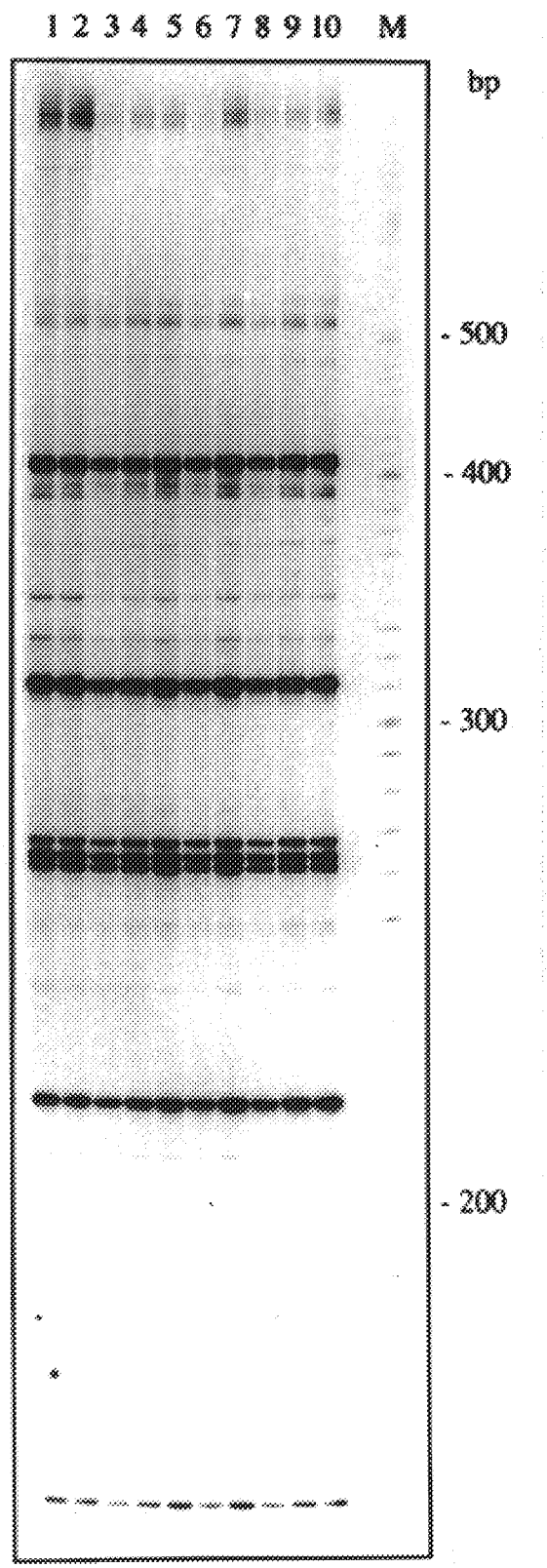
FIG. 4 shows the reproducibility of the method demonstrated by ten independent experiments.

A schematic representation of the reaction protocol carried out in example 3 is given in FIG. 3.

EXAMPLE 4

Comparison of the MADS Box Gene Expression between Teosinte and Maize

The DNA isolated in example 1 from female inflorescences of maize and Teosinte were converted into first strand cDNA as described in example 3 and used for the synthesis of amplification products of transcript-specific length. In this process a mixture of the oligonucleotides P038, P041, P042 and P043 which in this case carried a biotin group at their 5' end were used for the selective amplification of cDNA molecules that represent members of the MADS box gene family. After incubation with MseI as the restriction enzyme, the biotin-labelled extension products were separated by means of streptavidin-coated magnetic particles (Dynal) and used for the ligation of linkers as described in examples 2 and 3. Oligonucleotide P046 5'-(A/C)G(G/C) CAG GT(G/C) AC(C/G) T(A/T)C-3' (directed against "RQVT(F/Y)") was used for the reamplification. The amplification products obtained in this way were radioactively labelled as described and separated on a 6% sequencing gel.

EXAMPLE 5

Analysis and Identification of Amplification Products

The bands of interest were cut out of the gels obtained in example 3 and example 4. The nucleic acids contained therein were eluted in 25 μl TE buffer. In each case 5 μl eluate were reamplified in 30 cycles in a volume of 50 μl using the above-mentioned PCR conditions. The respective MADS box primers and the oligonucleotide LR21 which is identical to the bases 1–21 of LR32 were used as the primers. 0.5 μl of the reamplified bands were sequenced according to the instructions of the pmol cycle sequencing kit from Promega for the sequence analysis in which either LR32, the respective MADS box PCR primer used in each case or the internal MADS box primer P009 (5'-GAA GGC GTA CGA GCT CTC GGT GCT-3') was used as the primer. The annealing temperatures were 70° C. for LR32 and P009 and 50° C. for the other MADS box primers. The sequence information from the excised bands was then used to identify corresponding clones in cDNA libraries or genomiclibraries.

Figure 5:
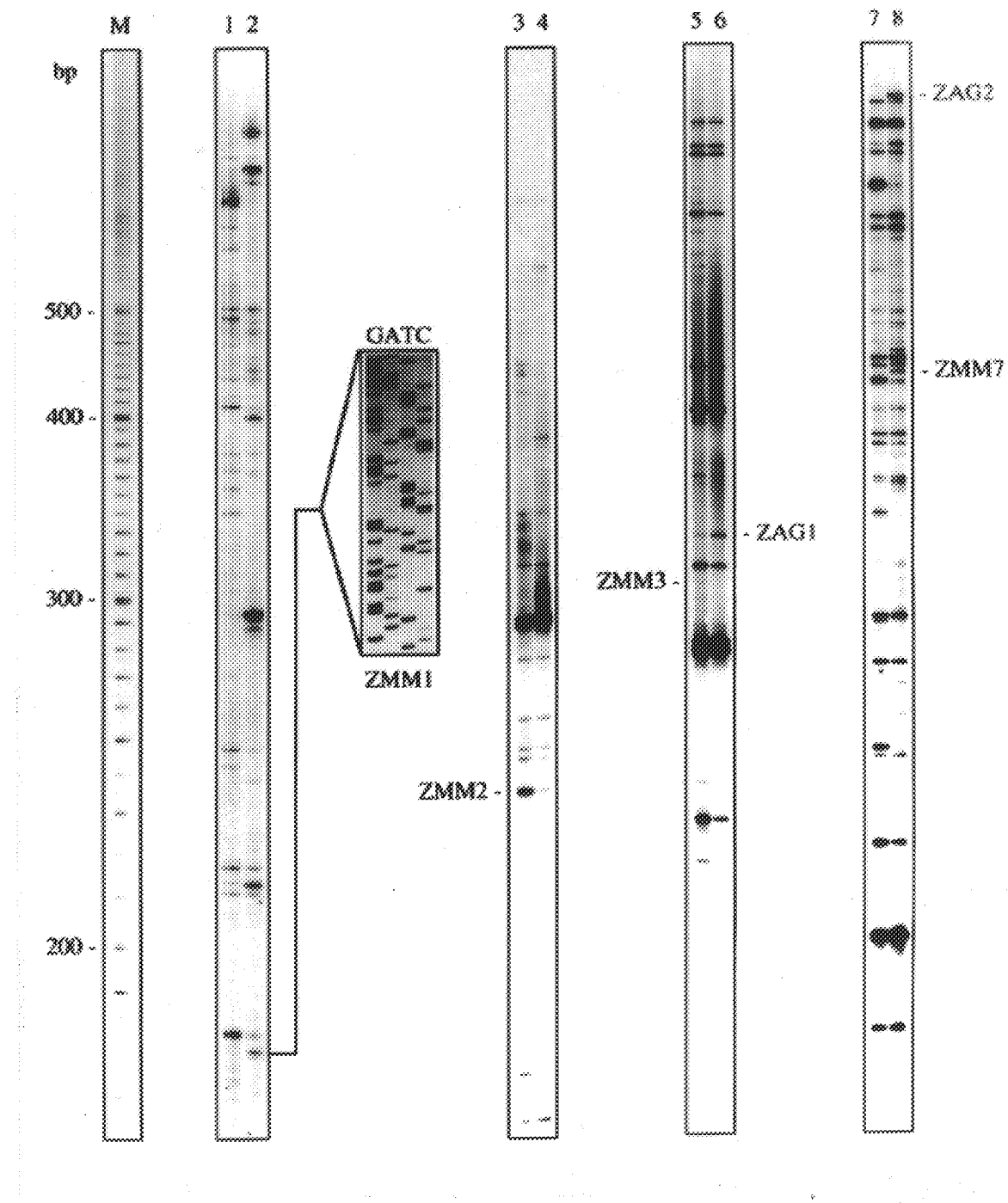
FIG. 5 shows the result of the isolation of differentially expressed MADS box genes using the method according to the invention.

The result of the isolation of sex-dependently expressed MADS box genes is shown in FIG. 5. The lanes with uneven numbers corresponded to transcripts from male inflorescences, the lanes with even numbers correspond to female transcripts. The gene ZMM1 was obtained using the primer P038 and restriction enzyme Sau3AI, the sequence ladder shows a part of the ZMM1 sequence which was obtained by direct sequencing of the excised and reamplified bands using LR32 as the sequencing primer. In order to identify ZMM2, the primer P042 and the enzyme HinfI were used. ZMM3 and ZAG1 were obtained using the primer P041 and MseI. ZMM7 and ZAG2 were obtained with the primer P043 and MseI. The lane denoted M represents the nucleic acid length marker.

A classification of genes identified by the method according to the invention is shown in FIG. 6. A comparison of 101 known sequences of MADS domains from yeast, animals and plants yielded the MADS domain consensus sequence given in line 1. Furthermore, different subfamilies were found which differ with regard to the entire gene sequence, expression pattern and their function. The MADS sequences from maize identified by the method according to the invention are members of two of these subfamilies, the. AG-like and the AGL2-like subfamily. The comparative sequences AGAMOUS (Yanofsky et al, Nature 346 (1990), 35–39) and AGL2 (Ma et al., Genes Dev. 5 (1991), 484–495) originate from *Arabidopsis thaliana* (At). The comparative sequences FBP6 (Angenent et al, Plant J. 4 (1993), 101–112) and FBP2 (Angenent et al, Plant Cell 4 (1992), 983–993) originate from *Petunia hybrida* (Ph). In addition TAG1 (Pnueli et al, Plant Cell 6 (1994), 163–167) and TM5 (Pnueli et al, Plant J. 1 (1991), 255–266) from *Lycopersicon esculentum* (Le) are stated as comparative sequences. In the present experiment the genes ZAG1, ZAG2, ZMM1 and ZMM2 (Schmidt et al), Plant Cell 5 (1993), 729–737; Theissen et al, Gene 156 (1995), 155–166) as well as further new sequences ZMM3 and ZMM7 from *Zea mays* (Zm) were identified. For the individual sequences of the MADS domain only deviations from the consensus sequence are stated in FIG. 6 in which the hyphens indicate identity with the consensus sequence. The underlined amino acids in the consensus sequence show the binding site for the gene family-specific primer.

In all six identified MADS box genes from maize it was possible to confirm the differential expression detected by the method according to the invention by independent Northern blot or in situ hybridization experiments. A comparison of the intensity of the bands of the amplification products with respective data from Northern blots shows that the method according to the invention enables at least a semi-quantitative determination of the expression of individual members of gene families in different samples.

Moreover the method according to the invention has a high reproducibility since 10 independent replicate experiments starting with cDNA resulted in exactly the same band pattern.

Altogether it was possible to identify six different MADS box genes by the method according to the invention of which 4 had already been known. Of the already known genes the expression of ZAG2 and ZMM1 was identified as being specific for female plants. ZAG1 is expressed more strongly in female plants than in male plants. In contrast ZMM2 is expressed more strongly in male than in female inflorescences.

The two new MADS box genes isolated by the method according to the invention are members of the subfamily of AGL2-like genes. One of these genes, named ZMM3, is more strongly expressed in male than in female inflorescences. In contrast the expression of the new gene ZMM7 seems to take place specifically in female plants.

I claim:

1. A method for the differential analysis of the expression of members of a gene family said method comprising:

(a) isolating mRNA molecules from at least one tissue sample to be analyzed, (b) synthesizing cDNA first strand molecules from the mRNA molecules using a cDNA primer, (c) preparing amplification products by selectively amplifying the cDNA first stand molecules of members of a gene family of interest using oligonucleotide primers comprising at least one gene family specific primer wherein said gene family specific primer is an oligonucleotide which hybridizes under PCR conditions with a conserved domain within the gene family of interest and a reverse primer which is an oligonucleotide directed against a sequence that is complementary to the sequence of the cDNA primer a reverse primer and labeling the amplification products, (d) transcript-specific shortening of the amplification products obtained in (c) by cleaving the amplification products with at least one restriction endonuclease, (e) separating the cleaved amplification products obtained in (d) according to their length and (f) analyzing the separated amplification products.

2. The method as claimed in claim 1, wherein the synthesis of the cDNA first strand molecules in step (b) is carried out by reverse transcription using an oligo-dT nucleotide as a cDNA primer.

3. The method as claimed in claim 2, wherein the oligo-dT primer has an extension at its 5' end or at its 3' end or at both its 5' and 3' ends.

4. The method as claimed in claim 1, wherein the cDNA primer is a random primer or a mixture of random primers.

5. The method as claimed in claim 1, wherein the cDNA primer is a gene family-specific primer or a mixture of gene family-specific primers.

6. The method as claimed in claim 1, wherein the cDNA primer is an oligo-dT primer with a 5' extension and the reverse primer in step (c) has a sequence which is directed against a sequence that is complementary to the sequence of the 5' extension.

7. The method as claimed in claim 1, wherein the restriction endonuclease cleaves the amplification products with a high statistical probability.

8. The method of claim 7, wherein the restriction endonuclease has a four-base recognition sequence.

9. The method as claimed in claim 1, wherein the label is incorporated by using a primer which carries a marker group.

10. The method as claimed in claim 1, wherein the label is incorporated by using labeled nucleotides in the amplification.

11. The method as claimed in claim 1, wherein label is incorporated into the amplification products by primer extension wherein said amplification products are templates.

12. The method as claimed in claim 1, wherein separating the amplification products is by gel electrophoresis.

13. The method as claimed in claim 1, wherein the analysis of the separated amplification products is by direct sequencing of said amplification products.

14. The method as claimed in claim 1, wherein the first strand cDNA molecules are provided with a specific nucleotide sequence at their 3' ends and an oligonucleotide directed against the specific nucleotide sequence is used as a reverse primer for the amplification in step (c).

15. The method as claimed in claim 14, wherein the specific nucleotide sequence comprises a homopolymer or an arbitrary sequence.

16. The method as claimed in claim 1, wherein the first strand cDNA molecules are converted into oligomeric or circular molecules or both oligomeric and circular molecules by self ligation and an oligonucleotide which is at least partially complementary to the cDNA primer is used as a reverse primer for the amplification in step (c).

17. The method of claim 16, wherein said oligonucleotide has an extension at its 3' end.

18. The method as claimed in claim 1, further comprising before step (c) and after step (b) converting the first strand of cDNA molecules into oligomeric or circular molecules or oligomeric and circular molecules by means of self-ligation and wherein two oligonucleotides directed against a sequence that is complementary to the sequence of the cDNA primer are used as primers for the amplification in step (c) wherein said oligonucleotides are in opposite orientation relative to each other.

19. The method of claim 18, wherein the oligonucleotide primers in (c) have 3' extensions.

20. The method as claimed in claim 1, wherein amplification steps are carried out under long range PCR conditions.

21. A method for isolating new genes comprising steps (a) to (f) of claim 1.

22. The method of claim 21 wherein the new genes are members of a gene family.

23. A method for determining the living stage of a cells or an organism comprising steps (a) to (f) of claim I.

24. A method for examining the life cycle of a cell or an organism comprising steps (a) to (f) of claim 1.

25. A method for the differential analysis of the expression of members of a gene family said method comprising:
   (a) isolating mRNA molecules from at least one tissue sample to be analyzed,
   (b) synthesizing cDNA first strand molecules from the mRNA molecules using a cDNA primer,
   (c) preparing amplification products by selectively amplifying the cDNA first strand molecules of members of a gene family of interest using at least one oligonucleotide gene family-specific primer wherein said gene family-specific primer is an oligonucleotide which hybridizes under PCR conditions with a conserved domain within the gene family of interest and a reverse primer which is an oligonucleotide directed against a sequence that is complementary to the sequence of the cDNA primer, and labeling the amplification products,
   (d) transcript-specific shortening of the amplification products obtained in (c)
   by cleaving the amplification products with at least one restriction endonuclease,
   (e) separating the cleaved amplification products obtained in (d) according to their length and
   (f) analyzing the separated amplification products.

26. The method as claimed in claim 25, wherein the linker molecule has a first end which is ligated to said cleaved amplification products and a second end which cannot be ligated to said cleaved amplification products.

27. The method as claimed in claim 25, wherein a nested primer is used in step (f) which is directed against the gene family-specific conserved domain.

28. The method as claimed in claim 25, wherein the amplification or reamplification products are isolated and additionally amplified.

29. The method as claimed in claim 28, wherein the oligonucleotide primer directed against the linker molecule and the gene-family specific primer in (f) are used in the additional amplification.

30. The method as claimed in claim 25, wherein the linker molecules, the cDNA primers or the amplification primers have at least one cleavage site for a restriction endonuclease.

31. The method as claimed in claim 25, wherein amplification steps are carried out under long range PCR conditions.

32. The method of claim 25, wherein the oligonucleotide primers in (d) have 3' extensions.

33. A method for the differential analysis of gene expression said method comprising:
   (a) isolating mRNA molecules from one or several samples to be analyzed,
      (aa) attaching an anchor sequence to the 5' end of the mRNA molecules,
   (b) synthesizing cDNA first strand molecules from the mRNA molecules,
   (c) amplifying the cDNA first strand molecules and labeling of the amplification products,
   (d) transcript-specific shortening of the amplification products by cleaving said amplification products with at least one restriction endonuclease,
   (e) separating the amplification products according to their length,
   (f) analyzing the separated amplification products.

34. The method as claimed in claim 33, wherein amplification steps are carried out under long range PCR conditions.

35. A method for the detection of transcripts, the method comprising:
   (a) isolating mRNA molecules from one or several samples,
      (aa) attaching of an anchor sequence to the 5' end of the mRNA molecules,
   (b) synthesizing cDNA first strand molecules from the mRNA molecules,
   (c) amplifying the cDNA first strand molecules,
   (d) transcript-specific shortening of the amplification products by cleaving said amplification products with at least one restriction endonuclease,
   (e) attaching linker molecules to the ends of the cleaved amplification products,
   (f) preparing a reamplification product by amplifying and labeling the cleaved amplification products having attached linkers in which a primer directed against the linker molecule attached in step (e) and a primer selected from the group consisting of (i) a primer directed against the anchor sequence attached in step (aa) or (ii) a primer directed against the cDNA primer sequence used in step (b) are used,
   (g) separating the reamplification products according to their length and,
   (h) detecting and analyzing the separated reamplification products.

36. The method of claim 35, further comprising before step (g) and after step (f),
   (ff) an additional amplification and labeling of the cleaved amplification products using nested primers, and
   (fff) a subtractive hybridization of two pools of amplification products which are to be compared with one another.

37. The method as claimed in claim 35, wherein amplification steps are carried out under long range PCR conditions.

38. The method of claim 35, wherein the oligonucleotide primers in (d) have 3' extensions.

39. A reagent kit for the analysis of the expression of genes comprising:

(a) an enzyme for cDNA first stand synthesis, (b) at least one enzyme for the synthesis of cDNA second strands and for the amplification of DNA fragments, (c) at least one double-stranded DNA linker molecule and an agent for attaching the linker molecule to the ends of DNA fragments, (d) single-stranded nucleic acid primer molecules comprising at least one of (i) a gene family-specific primer, (ii) a set of random primers, (iii) primers according to (i–ii) with a 3' extension or 5' extension or a 3' extension and a 5' extension, (iv) primers according to (i–iii) which carry marker groups and (v) primers according to (iv) which contain a 3' extension, (e) an agent for labeling and for detecting nucleic acids, (f) at least one oligo-dT nucleotide, and (g) at least one primer directed against a sequence which is complementary to the sequence of the DNA linker molecule.

40. The reagent kit of claim 39 further comprising at least one restriction enzyme.

41. The reagent kit of claim 40 further comprising reagents selected from the group consisting of RNase inhibitors, buffers, streptavidin-coated reaction vessels and magnetic particles.

42. A method for the detection of transcripts, said method comprising:

(a) isolating mRNA molecules from at least one tissue sample to be analyzed, (b) synthesizing cDNA first strand molecules from the mRNA molecules, (c) preparing double stranded cDNA from said cDNA first strand molecules, (d) cleaving said double stranded cDNA with at least one restriction endonuclease, (e) separating the cleaved double stranded cDNA according to their length, (f) attaching linker molecules to the ends of the cleaved amplification products obtained in (d), (g) preparing amplification products by amplifying and labeling the cleaved amplification products attached to said linker obtained in (f) using a linker primer and a primer directed against the cDNA primer or against a gene family-specific domain, and (h) detecting and analyzing the reamplification products.

43. The method as claimed in claim 42, wherein the double-stranded cDNA is produced by self-ligation of the first strand cDNA and subsequent second strand synthesis.

44. The method as claimed in claim 42, wherein amplification steps are carried out under long range PCR conditions.

45. The method of claim 35, wherein the oligonucleotide primers in (d) have 3' extensions.

46. A method for the detection of transcripts, said method comprising:

(a) isolating mRNA molecules from at least one tissue sample to be analyzed, (b) synthesizing cDNA first strand molecules from the mRNA molecules using a cDNA primer, (c) preparing amplification products by amplifying and labeling the cDNA first strand molecules using oligonucleotides comprising random primers, and labeling the amplification products, (d) cleaving said amplification products with at least one restriction endonuclease, (e) separating the amplification products according to their length, and (f) analyzing the separated amplification products.

47. The method as claimed in claim 46, wherein said random primers have a length of 15–25 nucleotides.

48. The method as claimed in claim 47, wherein the random primers have an adequately high degree of degeneracy in order to statistically bind to a DNA template as frequently as an 8–12 nucleotide long non-degenerate primer.

49. The method as claimed in claim 46, wherein amplification steps are carried out under long range PCR conditions.

50. A method for the detection of transcripts, said method comprising:

(a) isolating MA molecules from at least one tissue sample to be analyzed, (b) attaching an anchor oligonucleotide to the 5' end of said mRNA, (c) synthesizing cDNA first strand molecules from the mRNA molecules using a cDNA primer, (d) preparing amplification products by amplifying the cDNA first strand molecules using oligonucleotides comprising a primer which is a sequence which is complementary to the cDNA primer or a gene family-primer, (e) cleaving said amplification products with at least one restriction endonuclease, (f) attaching a linker molecule to the ends of the cleaved amplification products, (g) preparing reamplification products by amplifying and labeling the cleaved amplification products ligated to said linker using oligonucleotide primers comprising at least one primer selected from the group consisting of a gene family-specific primer, a primer which is directed against a sequence which is complementary to the sequence of the cDNA primer, a primer directed against the linker molecule and a primer directed against a sequence which is complementary to the sequence of the anchor oligonucleotide, (h) separating the reamplification products according to their length, and (i) detecting and analyzing the separated reamplification products.

51. The method as claimed in claim 50, wherein said anchor oligonucleotide is an RNA oligonucleotide and wherein the method further comprises after (a) and before (b) decapping the mRNA and wherein the RNA oligonucleotide is attached to the decapped mRNA molecules 5' ends by means of a single-strand ligation.

52. The method as claimed in claim 50, wherein said anchor oligonucleotide is an oligonucleotide which specifically hybridizes to the cap structure on said mRNA molecules and wherein said oligonucleotide has a nucleotide sequence which is incorporated into the first strand cDNA molecules during reverse transcription of said mRNA.

53. The method as claimed in claim 50, wherein amplification steps are carried out under long range PCR conditions.

54. The method as claimed in claim 50 further comprising before step (e) a subtractive hybridization step of the amplification products from two tissue samples which are to be compared with one another.

55. The method as claimed in claim 54, wherein the subtractive hybridization is carried out in several subpools which have been generated by using primers with different 3' extensions but otherwise identical sequence.

56. The method of claim 50, wherein the oligonucleotide primers in (d) have 3' extensions.

57. A method for the detection of transcripts, said method comprising:
(a) isolating mRNA molecules form at least one tissue sample to be analyzed,
(b) synthesizing cDNA first strand molecules from the mRNA molecules using a cDNA primer,
(c) adding said cDNA first strand molecules to an oligonucleotide having a known nucleotide sequence,
(d) preparing amplification products by amplifying the cDNA first strand molecules using at least one oligonucleotide primer directed against the oligonucleotide having a known nucleotide sequence in (b) and another oligonucleotide primer having a sequence that is directed against a sequence which is complementary to the cDNA primer in (c),
(e) cleaving said amplification products with at least one restriction endonuclease,
(f) separating the amplification products according to their length, and
(g) attaching linker molecules to the ends of the cleaved amplification products obtained in (d),
(h) preparing reamplification products by amplifying and labeling the cleaved amplification products attached to said linker obtained in (g) using an oligonucleotide primer selected from the group consisting of a gene family-specific primer, a primer directed against the linker, a primer directed against the sequence added to the cDNA and primer directed against a sequence which is complementary to the cDNA-primer,
(i) detecting and analyzing the separated amplification products.

58. The method as claimed in claim 57, wherein the oligonucleotide having a known nucleotide sequence comprises a homopolymer or an arbitrary sequence.

59. The method as claimed in claim 57, wherein the oligonucleotide having a known nucleotide sequence is modified at its 3' end in order to prevent further ligation of the oligonucleotides.

60. The method of claim 57, wherein the oligonucleotide primers in (d) have 3' extensions.

61. The method as claimed in claim 57, wherein amplification steps are carried out under long range PCR conditions.

62. A method for the differential analysis of the expression of members of a gene family said method comprising:
(a) isolating mRNA molecules from at least one tissue sample to be analyzed,
(b) attaching an anchor oligonucleotide to the 5' end of said mRNA molecules,
(c) synthesizing cDNA first strand molecules from the mRNA molecules using a cDNA primer,
(d) preparing amplification products by selectively amplifying the cDNA first stand molecules of members of a gene family using oligonucleotide primers comprising at least one gene family specific primer, wherein said gene family specific primer is an oligonucleotide which hybridizes under PCR conditions with a conserved domain within the gene family, and an oligonucleotide directed against a sequence which is complementary to the sequence of the anchor oligonucleotide functioning as a reverse primer, and labeling the amplification products,
(e) transcript specific shortening of the amplification products with at least one restriction endonuclease,
(f) separating the reamplification products according to their length, and
(g) analyzing the separated reamplification products.

63. The method as claimed in claim 62, wherein amplification steps are carried out under long range PCR conditions.

64. The method of claim 50 or 62 wherein said RNA oligonucleotide has a length of 20–30 bases.

65. A method for the detection of transcripts, said method comprising:
(a) isolating mRNA molecules from at least one tissue sample to be analyzed,
(b) synthesizing cDNA first strand molecules from the mRNA molecules using a cDNA primer,
(c) preparing amplification products by amplifying the cDNA first strand molecules using oligonucleotides comprising a primer which is directed against a sequence which is complementary to the cDNA primer or a gene family-primer,
(d) cleaving said amplification products with at least one restriction endonuclease,
(e) attaching a linker molecule to the ends of the cleaved amplification products,
(f) preparing reamplification products by amplifying and labeling the cleaved amplification products ligated to said linker using oligonucleotide primers comprising at least one primer selected from the group consisting of a gene family-specific primer, a primer which is directed against a sequence which is complementary to the sequence of the cDNA primer, a primer directed against the linker molecule and a primer directed against a sequence which is complementary to the sequence of the anchor oligonucleotide.
(g) separating the reamplification products according to their length, and
(h) detecting and analyzing the separated reamplification products.

66. A method for the detection of transcripts, said method comprising:
(a) isolating mRNA molecules from at least one tissue sample to be analyzed,
(b) synthesizing cDNA first strand molecules from the mRNA molecules,
(c) preparing double stranded cDNA from said cDNA first strand molecules,
(d) preparing amplification products by amplifying the double stranded cDNA,
(e) cleaving said double stranded cDNA with at least one restriction endonuclease,
(f) separating the cleaved double stranded cDNA according to their length,
(g) attaching linker molecules to the ends of the cleaved amplification products obtained in (d),
(h) preparing reamplification products by amplifying and labeling the cleaved amplification products attached to said linker obtained in (g) using a linker primer and a primer directed against the cDNA primer or against a gene family-specific domain, and
(i) detecting and analyzing the reamplification products.

67. A reagent kit for the analysis of the expression of genes comprising:
   (a) an enzyme for cDNA first strand synthesis,
   (b) at least one enzyme for the synthesis of cDNA second strands and for the amplification of DNA fragments,
   (c) at least one double-stranded DNA linker molecule and an agent for attaching the linker molecule to the ends of DNA fragments,
   (d) an RNA oligonucleotide and attaching agent,
   (e) an agent for labeling and for detecting nucleic acids,
   (f) a primer directed against a sequence which is complementary to the sequence of the RNA oligonucleotide,
   (g) at least one oligo-dT nucleotide, and
   (h) at least one primer derived from the sequence of the DNA linker molecule.

* * * * *

UNITED STATES PATENT AND TRADEMARK OFFICE
CERTIFICATE OF CORRECTION

PATENT NO. : 5,876,932  
DATED : March 2, 1999  
INVENTOR(S) : Achim Fischer

Page 1 of 1

It is certified that error appears in the above-identified patent and that said Letters Patent is hereby corrected as shown below:

In the title page under the title Assignee, line 73, change "Max-Planc" to read as --Max-Planck--.

Column 11,  
Line 54, insert a period after "sequence" to read as --sequence.--.

Column 12,  
Line 45, change "oligonucleotide,." to read as --oligonucleotide,--.  
Line 58, change "indended" to read as --intended--.

Column 15,  
Line 4, change "5Ml" to read as -- 5$\mu$ --.

Column 18,  
Line 15, change "the." to read as --the--.

Column 29,  
Line 61, change "stand" to read as --strand--.

Signed and Sealed this

Third Day of July, 2001

Attest:

NICHOLAS P. GODICI  
Attesting Officer  
Acting Director of the United States Patent and Trademark Office

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1:

CACGAUCUGA GGCCGAUCGA UUCA  24

( 2 ) INFORMATION FOR SEQ ID NO: 2:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 2:

ACCTACGTGC AGATTTTTTT TTTTTTTTV  29

( 2 ) INFORMATION FOR SEQ ID NO: 3:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 3:

CACGATCTGA GGCCGATCGA TTC  23

( 2 ) INFORMATION FOR SEQ ID NO: 4:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 4:

TCACATGCTA AGTCTCGCGA  20

( 2 ) INFORMATION FOR SEQ ID NO: 5:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 5:

GATCTCGCGA GACTTAGCAT GTGAC  25

( 2 ) INFORMATION FOR SEQ ID NO: 6:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 6:

GATCAAGMGS ATCGAGAA 18

( 2 ) INFORMATION FOR SEQ ID NO: 7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

GATGAAGMGS ATCGAGAA 18

( 2 ) INFORMATION FOR SEQ ID NO: 8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 8:

GATCAAGCAY ATCGAGAA 18

( 2 ) INFORMATION FOR SEQ ID NO: 9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 9:

GATCAAGAAG ATCGAGAA 18

( 2 ) INFORMATION FOR SEQ ID NO: 10:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 10:

ACTCGATTCT CAACCCGAAA GTATAGATCC CA 32

( 2 ) INFORMATION FOR SEQ ID NO: 11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 11:

TGGGATCTAT ACTTTCAA 18

( 2 ) INFORMATION FOR SEQ ID NO: 12:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

```
MGSCAGGTSA CSTWC                                                                   15
```

( 2 ) INFORMATION FOR SEQ ID NO: 13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 13:

```
GAAGGCGTAC GAGCTCTCGG TGCT                                                         24
```

( 2 ) INFORMATION FOR SEQ ID NO: 14:

( i ) SEQUENCE CHARACTERISTICS:
        ( A ) LENGTH: 60 amino acids
        ( B ) TYPE: amino acid
        ( C ) STRANDEDNESS:
        ( D ) TOPOLOGY: linear ( x i ) SEQUENCE DESCRIPTION: SEQ ID NO: 14:

```
Met Gly Arg Gly Lys Ile Glu Ile Lys Arg Ile Glu Asn Lys Thr Asn
 1               5                   10                  15

Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35              40                      45

Ser Ser Arg Gly Lys Leu Tyr Glu Tyr Ala Ser Asn
    50              55                  60
```